US010722655B2

(12) United States Patent
Folk et al.

(10) Patent No.: US 10,722,655 B2
(45) Date of Patent: Jul. 28, 2020

(54) AUTOINJECTOR WITH SHOCK REDUCING ELEMENTS

(71) Applicant: AMGEN INC., Thousand Oaks, CA (US)

(72) Inventors: Christopher Folk, Los Angeles, CA (US); Scott R. Gibson, Granada Hills, CA (US)

(73) Assignee: AMGEN INC., Thousand Oaks, CA (US)

( * ) Notice: Subject to any disclaimer, the term of this patent is extended or adjusted under 35 U.S.C. 154(b) by 91 days.

(21) Appl. No.: 15/302,116

(22) PCT Filed: May 6, 2015

(86) PCT No.: PCT/US2015/029485
§ 371 (c)(1),
(2) Date: Oct. 5, 2016

(87) PCT Pub. No.: WO2015/171777
PCT Pub. Date: Nov. 12, 2015

(65) Prior Publication Data
US 2017/0182253 A1 Jun. 29, 2017

Related U.S. Application Data

(60) Provisional application No. 61/990,063, filed on May 7, 2014.

(51) Int. Cl.
*A61M 5/31* (2006.01)
*A61M 5/315* (2006.01)
(Continued)

(52) U.S. Cl.
CPC ............ *A61M 5/3134* (2013.01); *A61M 5/20* (2013.01); *A61M 5/2033* (2013.01);
(Continued)

(58) Field of Classification Search
CPC ...... A61M 2005/2086; A61M 5/31511; A61M 5/2033; A61M 2005/206; A61M 2005/2013
See application file for complete search history.

(56) References Cited

U.S. PATENT DOCUMENTS 5,318,156 A 6/1994 Davis
5,957,886 A 9/1999 Weston
(Continued)

FOREIGN PATENT DOCUMENTS

BE 537349 A 4/1959
DE 102008044852 A1 3/2010
(Continued)

OTHER PUBLICATIONS

Written Opinion issued in Singaporean Patent Application No. 11201609219Q, dated Mar. 11, 2017.
(Continued)

*Primary Examiner* — Scott J Medway
(74) *Attorney, Agent, or Firm* — Marshall, Gerstein & Borun LLP

(57) ABSTRACT

An injection device, method, and system for drug delivery includes a primary container for storing a drug, the container having a stopper movably disposed in the container for expelling the drug, an injection drive mechanism comprising a plunger for acting on the stopper and an energy source for exerting a force on the plunger to cause the plunger to act on the stopper to expel the drug, the force causing the plunger to accelerate to a velocity prior to acting on the stopper, and a damping mechanism for reducing the velocity of the plunger prior to acting on the stopper. The damping mechanism can include a dashpot or an energy absorbing material associated with the plunger. Alternatively or additionally, the damping mechanisms can include absorbing material dis-
(Continued)

posed between support members of an outer casing of the injection device and the primary container.

32 Claims, 9 Drawing Sheets

(51) Int. Cl.
| | |
|---|---|
| *A61M 5/20* | (2006.01) |
| *F16F 9/36* | (2006.01) |
| *F16F 9/32* | (2006.01) |
| *F16F 9/16* | (2006.01) |
| *F16F 9/348* | (2006.01) |
| *A61M 5/32* | (2006.01) |

(52) U.S. Cl.
CPC ........... *A61M 5/31511* (2013.01); *F16F 9/16* (2013.01); *F16F 9/3228* (2013.01); *F16F 9/3481* (2013.01); *F16F 9/361* (2013.01); *A61M 5/3243* (2013.01); *A61M 2005/2086* (2013.01); *A61M 2005/3143* (2013.01)

(56) References Cited

U.S. PATENT DOCUMENTS

| | | |
|---|---|---|
| 6,171,286 B1 * | 1/2001 | Gross .................... A61M 5/315 604/218 |
| 6,258,068 B1 | 7/2001 | Kirchhofer et al. |
| 6,270,479 B1 | 8/2001 | Bergens et al. |
| 6,371,939 B2 | 4/2002 | Bergens et al. |
| 6,793,646 B1 | 9/2004 | Giambattista et al. |
| 7,128,728 B2 | 10/2006 | Kirchhofer et al. |
| 7,357,791 B2 | 4/2008 | Kirchhofer et al. |
| 7,449,009 B2 | 11/2008 | Eichhorst |
| 7,901,377 B1 | 3/2011 | Harrison et al. |
| 7,931,625 B2 | 4/2011 | Kirchhofer et al. |
| 7,967,772 B2 | 6/2011 | McKenzie et al. |
| 8,021,335 B2 | 9/2011 | Lesch, Jr. |
| 8,376,998 B2 | 2/2013 | Daily et al. |
| 8,409,138 B2 | 4/2013 | James et al. |
| 8,562,564 B2 | 10/2013 | Lesch, Jr. |
| 8,591,463 B1 | 11/2013 | Cowe |
| 8,641,669 B2 | 2/2014 | Renz et al. |
| 8,647,303 B2 | 2/2014 | Cowe |
| 9,061,103 B2 | 6/2015 | Kemp et al. |
| 9,119,920 B2 | 9/2015 | Cowe |
| 9,132,241 B2 | 9/2015 | Guillermo |
| 9,155,837 B2 | 10/2015 | Kemp et al. |
| 9,180,258 B2 | 11/2015 | Kemp et al. |
| 9,180,259 B2 | 11/2015 | Lesch, Jr. |
| 9,233,214 B2 | 1/2016 | Kemp et al. |
| 9,233,215 B2 | 1/2016 | Hourmand et al. |
| 9,457,149 B2 | 10/2016 | Kemp et al. |
| 9,474,859 B2 | 10/2016 | Ekman et al. |
| 9,486,581 B2 | 11/2016 | Lovell et al. |
| 9,925,337 B2 * | 3/2018 | Fourt .................. A61M 5/2033 |
| 2004/0024367 A1 | 2/2004 | Gilbert |
| 2005/0154346 A1 | 7/2005 | Green |
| 2006/0211982 A1 * | 9/2006 | Prestrelski ........... A61K 9/0014 604/60 |
| 2006/0287630 A1 | 12/2006 | Hommann |
| 2007/0167907 A1 | 7/2007 | Deslierres et al. |
| 2007/0265568 A1 | 11/2007 | Tsals et al. |
| 2008/0119783 A1 | 5/2008 | Green |
| 2008/0312592 A1 | 12/2008 | Barrow-Williams et al. |
| 2009/0247951 A1 | 10/2009 | Kohlbrenner et al. |
| 2010/0049125 A1 * | 2/2010 | James .................. A61M 5/2033 604/110 |
| 2011/0071477 A1 | 3/2011 | Guillermo |
| 2011/0288492 A1 * | 11/2011 | Holmqvist |
| 2013/0218093 A1 * | 8/2013 | Markussen ........... A61M 5/001 604/198 |
| 2013/0317447 A1 | 11/2013 | Cowe |
| 2014/0114250 A1 * | 4/2014 | DeSalvo .............. A61M 5/2053 604/143 |
| 2014/0148784 A1 | 5/2014 | Anderson et al. |
| 2014/0257191 A1 | 9/2014 | Cowe |
| 2015/0165129 A1 * | 6/2015 | Row ..................... A61M 5/482 604/189 |
| 2015/0209517 A1 | 7/2015 | Brunnberg et al. |
| 2016/0001004 A1 | 1/2016 | Fourt et al. |
| 2016/0008541 A1 | 1/2016 | Hirschel et al. |
| 2016/0008542 A1 | 1/2016 | Hirschel et al. |
| 2016/0022922 A1 | 1/2016 | Kemp et al. |
| 2016/0038679 A1 | 2/2016 | Guillermo |
| 2016/0067420 A1 | 3/2016 | Higgins et al. |
| 2016/0074584 A1 | 3/2016 | Carmel et al. |
| 2016/0106920 A1 | 4/2016 | Stefansen |
| 2016/0235924 A1 | 8/2016 | Soerensen et al. |

FOREIGN PATENT DOCUMENTS

| | | | |
|---|---|---|---|
| EP | 0956875 B1 | 8/2005 | |
| EP | 1439872 B1 | 9/2006 | |
| EP | 1586342 B1 | 1/2007 | |
| EP | 1586341 B1 | 1/2008 | |
| EP | 1762261 B1 | 4/2008 | |
| EP | 2218473 B1 | 8/2011 | |
| EP | 2364739 A1 | 9/2011 | |
| EP | 2364740 A1 | 9/2011 | |
| EP | 2364741 A1 | 9/2011 | |
| EP | 2399627 A1 | 12/2011 | |
| EP | 2399631 A1 | 12/2011 | |
| EP | 2438939 A1 | 4/2012 | |
| EP | 2468337 A1 | 6/2012 | |
| EP | 2468341 A1 | 6/2012 | |
| EP | 1680160 B1 | 7/2013 | |
| EP | 2665501 A1 | 11/2013 | |
| EP | 2716316 A1 | 4/2014 | |
| EP | 2742962 A2 | 6/2014 | |
| EP | 2968766 A1 | 1/2016 | |
| EP | 1907033 B1 | 8/2016 | |
| EP | 2983772 B1 | 2/2017 | |
| EP | 3017837 B1 | 2/2017 | |
| GB | 2424838 A | 10/2006 | |
| JP | 2011520540 A | 7/2011 | |
| KR | 10-2009-0122020 | 11/2009 | |
| WO | WO-03035149 A1 | 5/2003 | |
| WO | WO-2005025636 A2 | 3/2005 | |
| WO | WO-2005115516 A1 * | 12/2005 | .......... A61M 5/2033 |
| WO | WO-2010066590 A1 | 6/2010 | |
| WO | WO-2011096907 A1 | 8/2011 | |
| WO | WO-2012098371 A1 | 7/2012 | |
| WO | WO-2014159017 A1 | 10/2014 | |

OTHER PUBLICATIONS

International Search Report for PCT/US2015/029485, dated Jul. 30, 2015.
European Patent Application No. 15724142.3, Communication Pursuant to Article 94(3) EPC, dated Jun. 28, 2019.
Chinese Patent Application No. 201580022028.8, Office Action, dated Jan. 30, 2019.
Japanese Patent Application No. 2016-566215, Second Office Action, dated Aug. 6, 2019.
Japanese Patent Application No. 2016-566215, Notice of Rejection, dated Jan. 29, 2019.
Israel Patent Application No. 247935, Office Action, dated Jan. 6, 2020.

\* cited by examiner

AUTOINJECTOR WITH SHOCK REDUCING ELEMENTS

CROSS-REFERENCE TO RELATED APPLICATION

This is the United States national phase of International Patent Application No. PCT/US2015/029485, having an international filing date of May 6, 2015, and which claims the priority benefit of U.S. Provisional Patent Application No. 61/990,063, filed May 7, 2014. The contents of each of the foregoing is expressly incorporated herein by reference in the entirety.

FIELD OF THE INVENTION

The present disclosure relates to injection devices for drug delivery. More particularly, the present disclosure relates to injection devices for drug delivery that include damping mechanisms that reduce shock during the operation of the injection devices.

BACKGROUND OF THE INVENTION

Autoinjectors and on-body injectors offer several benefits in delivery of therapeutics. One of the benefits can include simplicity of use, as compared with traditional methods of delivery using, for example, conventional syringes.

Many injector systems use coil and other spring structures to provide actuation energy for functions such as needle insertion and fluid delivery. The use of springs can offer benefits of simplicity and low cost, but can have certain limitations.

There is a linear relationship between force and displacement in spring actuators. To provide sufficient energy for drug delivery at the end of plunger stroke, an excessive amount of energy may be input to the system as drug delivery commences.

Further, as higher viscosity drugs are delivered via autoinjectors, the requisite spring forces will likely increase. Springs with higher spring constants transmit more force to the drug product and primary container. Because kinetic energy is proportional to velocity squared, even incremental increases in the spring constant can result in large changes in the net kinetic energy applied to the drug and primary container.

The patient may feel this excessive energy as a "slap" or similar physical "bump", as the spring driven plunger impacts the stopper of the primary container storing the drug. It is known that such mechanical bumps can also be distracting or disturbing to users of the injectors and can therefore prevent proper dose completion. It is therefore desirable to eliminate such disturbances.

It is further known that the "slap" and "bump" generated by the excessive energy can cause catastrophic effects, such as breakage of the primary container and drug product damage cause by shear load. Furthermore, high force springs can produce high shear rates on the drug product. In some cases, this high shear rate is undesireable.

Accordingly, an autoinjector is needed that can maintain the intended spring force load while reducing the velocity of the plunger before impact with the stopper of the primary container. Such an autoinjector may be potentially more comfortable and safer to use, and applicable to a greater range of drugs.

SUMMARY OF THE INVENTION

Disclosed herein are an injection device, and methods and systems for drug delivery. Within this disclosure, reference may be made to "autoinjectors"; however, such reference should also be understood to refer to on-body injectors where the description is applicable. In various embodiments, the device may comprise a container or reservoir for storing a drug, the container comprising a stopper movably disposed in the container for expelling the drug, an injection drive mechanism comprising a plunger for acting on the stopper, and an energy source for exerting a force on the plunger to cause the plunger to act on the stopper to expel the drug, the force causing the plunger to accelerate to a velocity prior to acting on the stopper, and a damping mechanism for reducing the velocity of the plunger prior to acting on the stopper, the damping mechanism comprising a housing, a piston assembly movable in the housing and acted upon by the plunger, and a working fluid displaceable by the piston assembly for resisting movement of the plunger. The container or reservoir may contain a drug or medicament and can be a cartridge or prefilled syringe.

In various other embodiments, the device may comprise a container for storing a drug, the container comprising a stopper movably disposed in the container for expelling the drug, an injection drive mechanism comprising a plunger for acting on the stopper and an energy source for exerting a force on the plunger to cause the plunger to act on the stopper to expel the drug, the force causing the plunger to accelerate to a velocity prior to acting on the stopper, and a damping mechanism for reducing the velocity of the plunger prior to acting on the stopper, the damping mechanism comprising energy absorbing material disposed on the plunger.

In still further embodiments, the injection device may comprise a container for storing a drug, the container comprising a stopper movably disposed in the container for expelling the drug, an injection drive mechanism comprising a plunger for acting on the stopper and an energy source for exerting a force on the plunger to cause the plunger to act on the stopper to expel the drug, the force causing the plunger to accelerate to a velocity prior to acting on the stopper, an outer casing for encasing the container, the outer casing including at least one support member for holding container within the outer casing and a damping mechanism for reducing energy applied by the energy source to the container, the damping mechanism comprising absorbing material disposed between the at least one support member and the container and/or the outer casing and the container.

BRIEF DESCRIPTION OF THE DRAWINGS

Like reference numerals are used in the drawings to identify like or similar elements and structures in the various embodiments.

DETAILED DESCRIPTION

Figure 1:
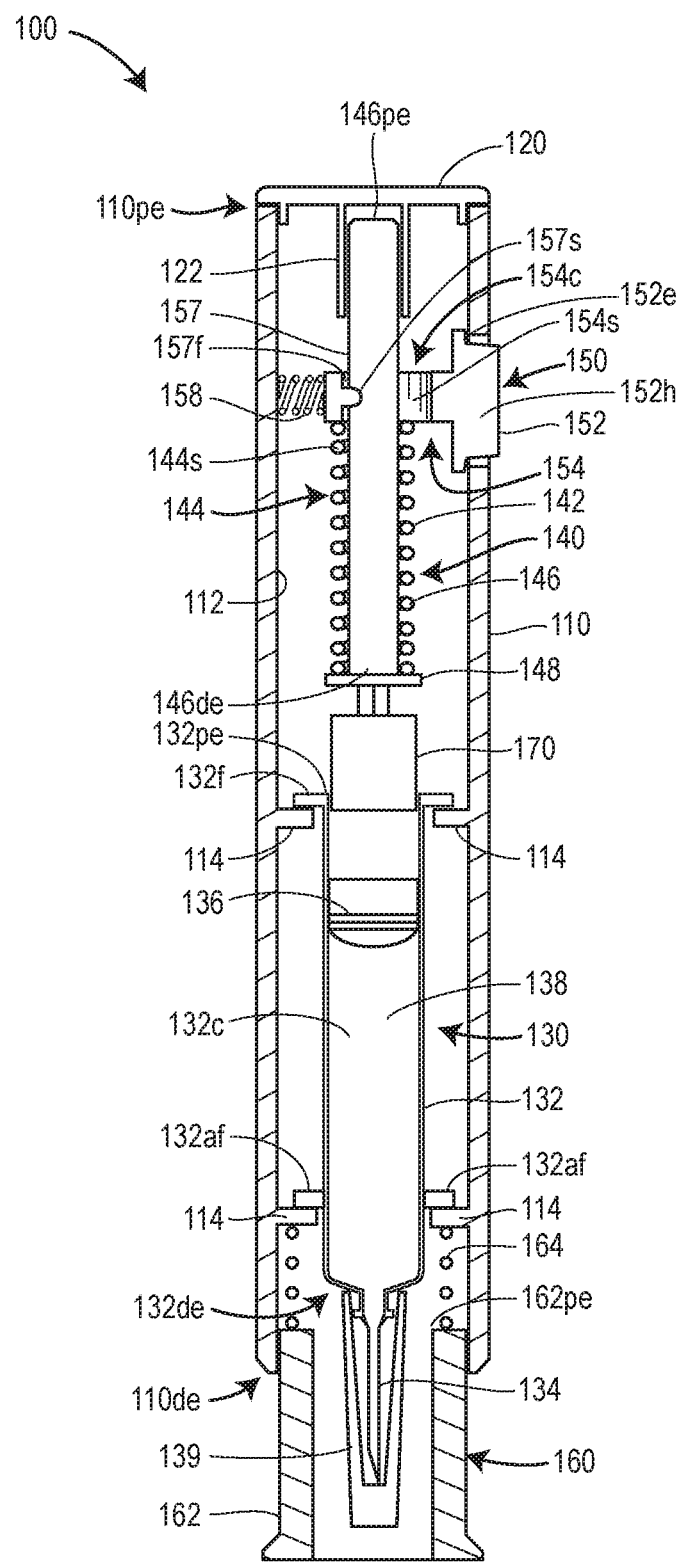
FIG. 1 is an elevational view in partial cross-section of an exemplary embodiment of an injection device for drug delivery, according to the present disclosure.

Disclosed herein is an injection device for drug delivery. In one embodiment, the injection device comprises a container for storing a drug, the container comprising a stopper movably disposed in the container for expelling the drug; an injection drive mechanism comprising a plunger for acting on the stopper and an energy source for exerting a force on the plunger to cause the plunger to act on the stopper to expel the drug, the force causing the plunger to accelerate to a velocity prior to acting on the stopper; and a damping mechanism for reducing the velocity of the plunger prior to acting on the stopper, the damping mechanism comprising a housing, a piston assembly movable in the housing and acted upon by the plunger, and a working fluid displaceable by the piston assembly for resisting movement of the plunger.

In some embodiments, the energy source comprises one or more springs.

In some embodiments, the energy source comprises a gas pressure or gas releasing arrangement.

In some embodiments, the damping mechanism is disposed between the stopper and the plunger.

In some embodiments, the damping mechanism is disposed at an end of the plunger, which is opposite to the stopper.

In some embodiments, the damping mechanism is integral with the plunger.

In some embodiments, the piston assembly includes a piston and a rod for pushing or pulling the piston.

In some embodiments, the piston assembly includes a disc-shaped piston.

In some embodiments, the piston is rigid.

In some embodiments, the piston includes at least one constriction.

In some embodiments, the at least one constriction is in a peripheral edge of the piston.

In some embodiments, the at least one constriction is in the piston.

In some embodiments, the injection device further comprises a constriction between the peripheral edge of the piston and the housing.

In some embodiments, the piston is resilient.

In some embodiments, the piston is porous.

In some embodiments, the piston assembly includes a disc-shaped piston and a rod for pushing or pulling the piston.

In some embodiments, the piston assembly includes a piston comprising two or more disc-shaped members.

In some embodiments, the disc-shaped members are rigid.

In some embodiments, each of the disc-shaped members includes at least one constriction.

In some embodiments, the at least one constriction is in a peripheral edge of at least one of the disc-shaped members.

In some embodiments, the at least one constriction is in at least one of the disc-shaped members.

In some embodiments, the injection device further comprises a constriction between the peripheral edge of at least one of the members and the housing.

In some embodiments, the disc-shaped members are resilient.

In some embodiments, the disc-shaped members are porous.

In some embodiments, the piston assembly includes a piston and a rod for pushing or pulling the piston, the piston comprising two or more disc-shaped members.

In some embodiments, the piston assembly includes a piston comprising a bellows structure.

In some embodiments, the bellows structure includes at least two lobes and a constriction for allowing the working fluid to flow between the two lobes.

In some embodiments, the piston assembly includes a piston and a rod for pushing or pulling the piston, the piston comprising a bellows structure.

In some embodiments, the bellows structure includes at least two lobes and a constriction for allowing the working fluid to flow between the two lobes.

In some embodiments, the rod is hollow to allow the working fluid to be exhausted from the bellows structure.

In some embodiments, the rod is hollow to allow the working fluid to be exhausted from the bellows structure.

In some embodiments, the container further comprises a dose delivery member.

In some embodiments, the dose delivery member comprises an injection needle.

In some embodiments, the injection device further comprises a triggering mechanism for activating the injection drive mechanism.

In some embodiments, the injection device further comprises a guard mechanism for preventing contact with the dose delivery member.

In some embodiments, the injection device further comprises an outer casing for encasing the container, the outer casing including at least one support member for holding container within the outer casing, and energy absorbing material disposed between the at least one support member and the container.

In some embodiments, the injection device further comprises an outer casing for encasing the container, and energy absorbing material disposed between the outer casing and the container.

In some embodiments, the energy absorbing material comprises a layer of damping material.

In some embodiments, the energy absorbing material comprises a laminate formed by two or more layers of damping material.

In some embodiments, layers of the laminate can have the same or different damping characteristics.

In another embodiment, the injection device comprises a container for storing a drug, the container comprising a stopper movably disposed in the container for expelling the drug; an injection drive mechanism comprising a plunger for acting on the stopper and an energy source for exerting a force on the plunger to cause the plunger to act on the stopper to expel the drug, the force causing the plunger to accelerate to a velocity prior to acting on the stopper; and a damping mechanism for reducing the velocity of the plunger prior to acting on the stopper, the damping mechanism comprising the energy absorbing material disposed on the plunger.

In another embodiment, the injection device comprises a container for storing a drug, the container comprising a stopper movably disposed in the container for expelling the drug; an injection drive mechanism comprising a plunger for acting on the stopper and an energy source for exerting a force on the plunger to cause the plunger to act on the stopper to expel the drug, the force causing the plunger to accelerate to a velocity prior to acting on the stopper; an outer casing for encasing the container; and a damping mechanism for reducing energy applied by the energy source to the container, the damping mechanism comprising the absorbing material disposed between the outer casing and the container.

In some embodiments, the outer casing includes at least one support member for holding the container within the outer casing, wherein the energy absorbing material is disposed between the at least one support member and the container.

In some embodiments, the injection device further comprises an outer casing, a sleeve disposed within the outer casing, the container mounted in the sleeve, and a first strip of energy absorbing or damping material disposed between the container and the sleeve at a location where the container and the sleeve contact one another.

In some embodiments, the sleeve includes a container support flange and the container includes a rim flange, the first strip of energy absorbing or damping material disposed between the container support flange and the rim flange.

In some embodiments, the injection device further comprises a second strip of energy absorbing or damping material disposed between the sleeve and the outer casing at a location where the sleeve and the outer casing contact one another.

In some embodiments, the sleeve includes a casing engagement flange and the outer casing includes a support member, the second strip of energy absorbing or damping material disposed between the casing engagement flange and the support member.

In some embodiments, the injection device further comprises a drug stored in the container.

In some embodiments, the drug is selected from the group consisting of TNF inhibitors, antibodies to the calcitonin gene-related peptide receptor, colony stimulating factors, erythropoiesis stimulating agents, apelin receptor agonists, anti-thymic stromal lymphopoietin antibodies, anti-thymic stromal lymphopoietinreceptor antibodies, antibodies that bind human Proprotein Convertase Subtilisin/Kexin Type 9 and tissue inhibitors of metalloproteinases.

Further disclosed herein is a method for administering a drug. The method comprises providing a container containing a drug and a stopper movably disposed in the container for expelling the drug; acting on the stopper with a plunger driven by an energy source that exerts a force on the plunger, the force causing the plunger to accelerate to a velocity prior to acting on the stopper; and reducing the velocity of the plunger with a damping mechanism prior to acting on the stopper, the damping mechanism comprising a piston assembly movable in a housing and acted upon by the plunger, and a working fluid displaceable by the piston assembly for resisting movement of the plunger.

In some embodiments, the drug is selected from the group consisting of TNF inhibitors, antibodies to the calcitonin gene-related peptide receptor, colony stimulating factors, erythropoiesis stimulating agents, apelin receptor agonists, anti-thymic stromal lymphopoietin antibodies, anti-thymic stromal lymphopoietinreceptor antibodies, antibodies that bind human Proprotein Convertase Subtilisin/Kexin Type 9 and tissue inhibitors of metalloproteinases.

FIG. 1 shows an exemplary embodiment of an injection device 100 according to the present disclosure. The injection device 100 can be adapted as a single-use, disposable injector or a multiple-use, reusable injector. The injection device 100 can be adapted to deliver any suitable medicament or drug including those having a high viscosity. The injection device 100 can be used by a caregiver or formally-trained healthcare provider to administer an injection. In addition, the injection device 100 can be adapted for use as an autoinjector for self-administration.

Referring to FIG. 1, the injection device 100 can include an elongated housing or outer casing 110. The injection device 100 can further include one or more of a drug storage device 130 (e.g., a syringe), an injection drive mechanism 140, a drive triggering mechanism 150, a guard mechanism 160, or a drive damper mechanism 170, each enclosed in the outer casing 110.

The outer casing 110 can be a single, unitary component or a multiple component assembly. As shown in FIG. 1, the outer casing 110 has an interior surface 112 that can include one or more support members 114 fixedly disposed thereon for holding the drug storage device 130 in a fixed manner within the outer casing 110. In some embodiments, one or more of the support members 114 may comprise a continuous, annular ledge or shelf. In other embodiments, one or more of the support members 114 may be formed as two or more coplanar ledges or shelf segments.

In some embodiments, one or more of the support members 114 may be configured as a carrier for the drug storage device 130. The carrier can be configured and adapted to axially move and/or allow the drug storage device 130 to move relative to the outer casing 110 to insert a dose delivery member 134 associated with the drug storage device 130 into the body of a user or patient after the injection device 100 has been appropriately positioned on the body at a selected injection site.

Referring still to FIG. 1, the drug storage device 130 can include a primary container 132, a dose delivery member 134, which can be an injection needle, cannula or any other fluid dispensing element suitable for injecting a drug into the body, and a stopper 136. The primary container 132 may be an elongated member having a closed distal end 132*de* with an opening (not visible), and an open proximal end 132*pe*. The primary container 132 can further include an interior chamber 132*c* for storing one or more doses of a medicament or drug 138. In some embodiments, the interior chamber 132*c* of the primary container 132 may be prefilled with the one or more doses of the medicament or drug 138. The primary container 132 can include a rim flange 132*f* disposed at or adjacent to the open proximal end 132*pe*. In some embodiments, the flange 132*f* can extend outwardly from an outer surface of the primary container 132. The flange 132*f* can engage one of the support members 114 disposed on the interior surface 112 of the outer casing 110. In some embodiments, the primary container 132 can include additional flanges 132*af* disposed between the distal end 132*de* and the proximal end 132*pe* of the primary container 132. One or more of the additional flanges 132*af* can extend outwardly from an outer surface of the primary container 132 and engage one or more of the support members 114 disposed on the interior surface 112 of the outer casing 110. In some embodiments, the closed distal end 132*de* of the primary container 132 may engage one or more of the support members (not shown) disposed on the interior surface 112 of the outer casing 110.

As shown in FIG. 1, the dose delivery member 134 can be disposed at the distal end 132*de* of the primary container 132 in fluid communication with the interior chamber 132*c* of the primary container 132, for delivering a dose of the medicament or drug 138. A removable shield 139 can be installed over the dose delivery member 134 for maintaining a sterile state prior to use of the injection device 100. In embodiments where the support members 114 are fixed relative to the outer casing 110, the dose delivery member 134 may extend through an opening at a distal end of the outer casing 110.

Still referring to FIG. 1, the stopper 136 of the drug storage device 130 can be disposed in the interior chamber 132*c* of the primary container 132 so that it is axially moveable relative to the primary container 132 for expelling the medicament or drug 138 through the dose delivery member 134. In some embodiments, the drug storage device 130 may comprise a conventional glass or plastic syringe or cartridge.

The guard mechanism 160 prevents the user or patient from contacting the dose delivery member 134 when the injection device 100 is not being used to administer an injection. As shown in FIG. 1, the guard mechanism 160 includes a guard member 162 movably disposed at the distal end 110*de* of the outer casing 110, and a retaining arrangement 164 that holds the guard member 162 in an extended position when the injection device 100 is not in use and allows the guard member 162 to retract toward the outer casing 110 when the injection device 100 is pressed toward the body of the patient at the injection site. The guard member 162 remains in an extended position relative to the outer casing 110 via the retaining arrangement 164 when the injection device 100 is not being used to administer an injection, thereby surrounding or covering the dose delivery member 134. The guard member 162 also retracts toward the outer casing 110 when the injection device 100 is pressed toward the body of the patient at the injection site to allow the dose delivery member 134 to penetrate the body. The guard member 162 may have a tubular configuration or any other suitable configuration that is capable of preventing the user or patient from contacting the dose delivery member 134 when the guard member 162 is in an extended position. The retaining arrangement 164 can include a coil spring or any other suitable mechanism that is capable of holding the guard member 162 in the extended position and allows the guard member 162 to retract toward the outer casing 110 when the injection device 100 is pressed toward the body of the patient at the injection site. The guard mechanism 160 can be configured so that the guard member 162 slides into or over the distal end 110*de* of the outer casing 110 during retraction of the guard mechanism 160. The retaining arrangement 164 may be disposed between the proximal end 162*pe* of the guard member 162 and a portion of the outer casing 110 (e.g., one or more of the support members 114 fixedly disposed on the interior surface 112 of the outer casing 110).

As shown in FIG. 1, the injection drive mechanism 140 can include a plunger 142 and an energy source 144 for propelling the plunger 142 into the drug storage device 130 to perform the injection, or both dose delivery member 134 insertion (e.g., embodiments where the drug storage device 130 is adapted to axially move relative to the outer casing 110) and injection. The plunger 142 can include a rod member 146 (or plunger rod 146) having distal and proximal ends 146*de* and 146*pe*, respectively. The plunger 142 can further include a head member 148 (or plunger head 148) disposed at the distal end 146*de* thereof.

The energy source 144 can comprise one or more spring elements. As depicted in FIG. 1, in some embodiments, one or more of the spring elements can comprise a coil spring 144*s*. The rod member 146 of the plunger 142 can extend through the coil spring 144*s* so that one end of the spring 144*s* engages the head member 148 and the other end of the spring 144*s* engages the drive triggering mechanism 150. Prior to operation of the injection device 100, the coil spring 144*s* is compressed between the head member 148 of the plunger 142 and the drive triggering mechanism 150, thereby generating a spring biasing force against the head member 148 and the drive triggering mechanism 150. When the injection device 100 is operated by activating the drive triggering mechanism 150, as explained in further detail herein, the coil spring 144*s* expands distally, thereby propelling the plunger 142 into the drug storage device 130 to drive the stopper 136 through the primary container 132 to expel the drug 138 through the dose delivery device 134.

In other embodiments, the energy source 144 can alternatively or further include a gas pressure or gas releasing arrangement. The energy provided by gas pressure or gas releasing arrangement operates on the plunger 142 to propel it into the drug storage device 130, thereby driving the stopper 136 through the primary container 132 to expel the drug 138 through the dose delivery device 134.

Referring still to FIG. 1, in some embodiments, the open, proximal end 110*pe* of the outer casing 110 may include a cap 120. The cap 120 may be unitary with the outer casing 110 or a separate member that has been fixedly attached to the proximal end 110*pe* of the outer casing 110. The cap 120 can include a tubular support member 122, which slidably supports proximal end 146*pe* of the plunger rod 146 when the plunger 142 is in a proximal-most axial position relative to the outer casing 110 (i.e., when the injection device 100 is armed or in a ready-to-use mode).

As shown in FIG. 1, the drive triggering mechanism 150 can include a button member 152, a plunger release member 154, and a trigger biasing member 158. The button member 152 allows the drive triggering mechanism 150 to be actuated to administer an injection with the injection device 100. The button member 152 can include a head portion 152*h* surrounded by a peripheral edge portion 152*e*. The head portion 152*h* extends above the peripheral edge portion 152*e* so that it can project through an aperture formed in the outer casing 110 when the peripheral edge portion 152*e* contacts the interior surface 112 of the outer casing 110 to allow actuation of the button member 152 by a user. The plunger release member 154 can project from a bottom or inner surface of the button member 152. In some embodiments, the plunger release member 154 can include a plunger cut-out 154*c* that is configured to define an elongated C-shaped surface 154*s*. The upper portion of the C-shaped surface 154*s* can include a first member 157*f* of a detent or latch arrangement 157, which cooperates with a corresponding second member 157s provided on an outer surface of the plunger rod 146. The trigger biasing member 158 forces the peripheral edge of the button member 152 against the interior surface 112 of the outer casing 110 so that the head portion 152h of the button member 152 extends through the button aperture of the outer casing 110 when the button member 152 of the drive triggering mechanism 150 is not pressed (i.e., activated). This, in turn, forces the first and second members 157f, 157s of the detent or latch arrangement 157 to remain engaged with one another, thereby retaining the plunger 142 in the proximal-most axial position relative to the outer casing 110 (i.e., the injection device 100 in the armed or ready-to-use mode), which as shown in FIG. 1, compresses the coil spring 144s between the head member 148 of the plunger 142 and the plunger release member 154. The trigger biasing member 158 can comprise a coil spring or any other suitable device for biasing the button member 152 against the interior surface 112 of the outer casing 110 when the button member 152 is not pressed.

After inserting the dose delivery member 134 into the body, the user or patient presses the button member 152 of the drive triggering mechanism 150 down into the outer casing 110 against the trigger biasing member 158 to actuate the injection drive mechanism 140 to administer an injection; the plunger release member 154 moves laterally within the outer casing 110, thereby disengaging the first and second members 157f, 157s of the detent or latch arrangement 157 from one another. This, in turn, releases the plunger 142 and allows the energy source 144 to propel the plunger 142 into the drug storage device 130 to drive the stopper 136 through the primary container 132 to expel the drug 138 through the dose delivery device 134.

Referring still to FIG. 1, the drive damper mechanism 170 reduces the velocity of the plunger 142 while retaining the intended force of the injection drive mechanism 140, before the plunger 142 begins to move the stopper 136 distally through the primary container 132. By reducing the velocity of the plunger 142, the drive damper mechanism 170 essentially operates as a shock reducing element, as it reduces the kinetic energy applied to the drug 138 and the drug storage device 130. The drive damper mechanism 170 can be adapted to reduce the velocity of the plunger 142 to ensure that pressure delivered to the system does not induce syringe breakage, pressure delivered to the system prevents appreciable "slap" or discomfort to the patient, and/or pressure delivered to the drug 138 prevents shear forces from damaging the drug 138.

In some embodiments, the drive damper mechanism can be adapted to reduce the velocity of the plunger by less than 1%. In other embodiments, the drive damper mechanism can be adapted to reduce the velocity of the plunger by about 1-5%. In further embodiments, the drive damper mechanism can be adapted to reduce the velocity of the plunger by about 5-10%. In further embodiments, the drive damper mechanism can be adapted to reduce the velocity of the plunger by about 10-15%. In further embodiments, the drive damper mechanism can be adapted to reduce the velocity of the plunger by about 15-20%. In further embodiments, the drive damper mechanism can be adapted to reduce the velocity of the plunger by about 20-30%. In still further embodiments, the drive damper mechanism can be adapted to reduce the velocity of the plunger by about 30-50%. In yet further embodiments, the drive damper mechanism can be adapted to reduce the velocity of the plunger by about 51%-100%. The reduction in velocity provided by the drive damper mechanism can be selected to prevent a physical disturbance and/or discomfort to the patient by preventing appreciable "slap", and/or reduce breakage of the drug storage device, and/or reduce drug product damage caused by shear load, and/or allow the injection device to be used for injecting drugs with higher viscosities.

Figure 4A:
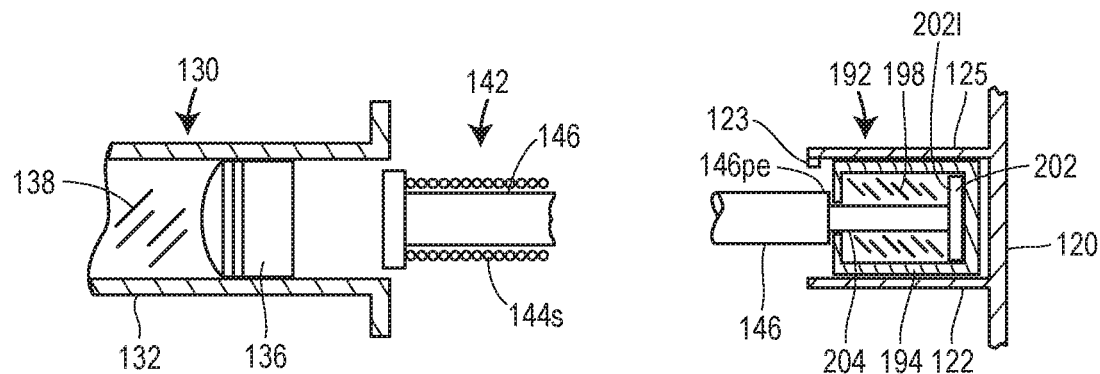
FIGS. 4A-4C are cross-sectional side views of another dashpot similar to that shown in FIG. 2, implemented in the injection device according to another embodiment of the present disclosure and depicting an exemplary mode of operation of the dashpot and the injection device.
Figure 4B:
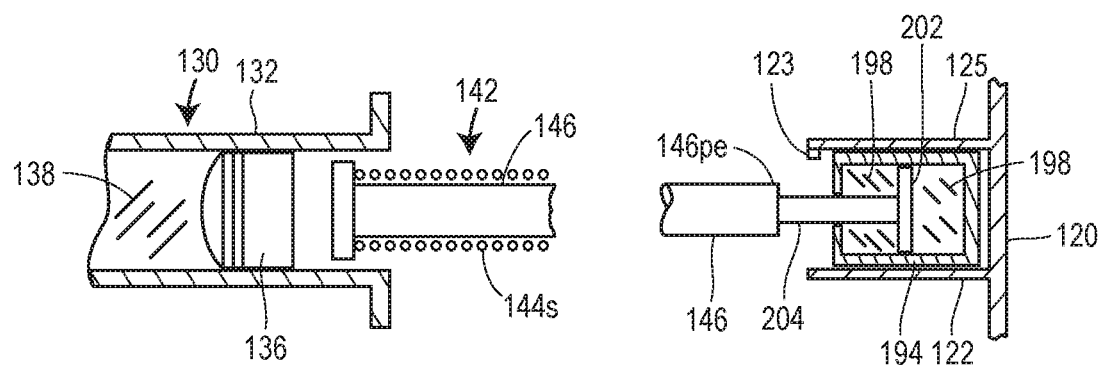
Figure 4C:
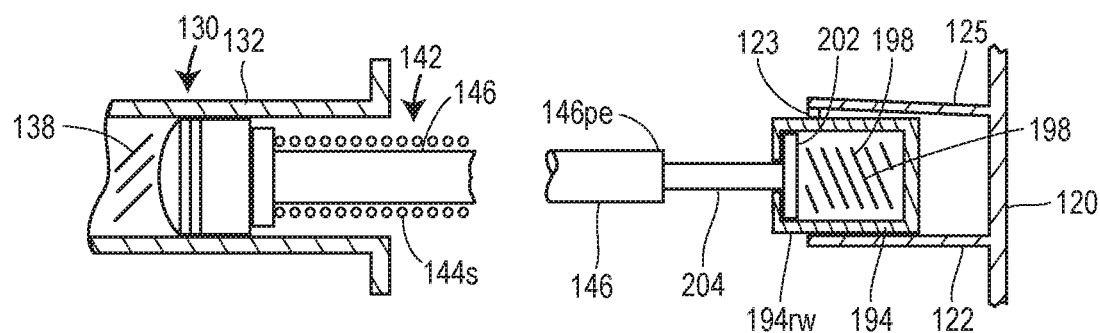
Figure 5A:
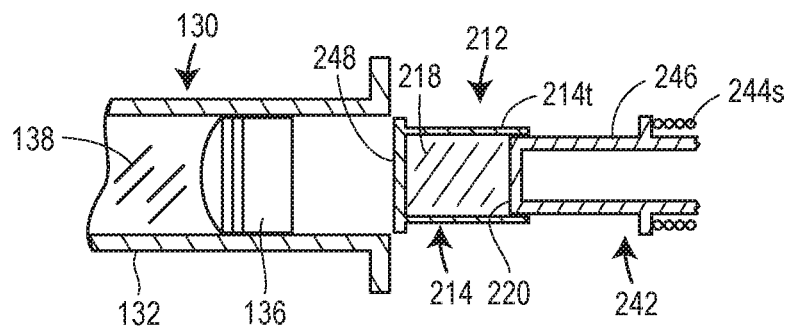
FIGS. 5A-5C are cross-sectional side views of another embodiment of the dashpot of the present disclosure and depicting an exemplary mode of operation of the dashpot and the injection device.
Figure 5B:
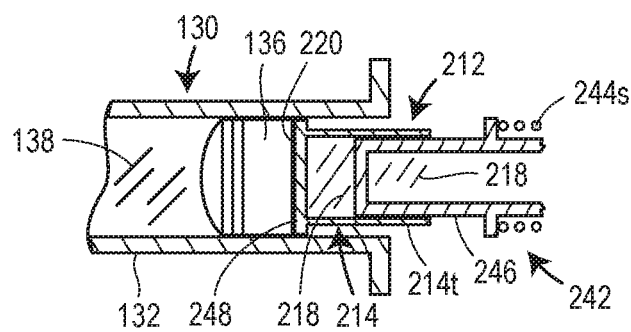
Figure 5C:
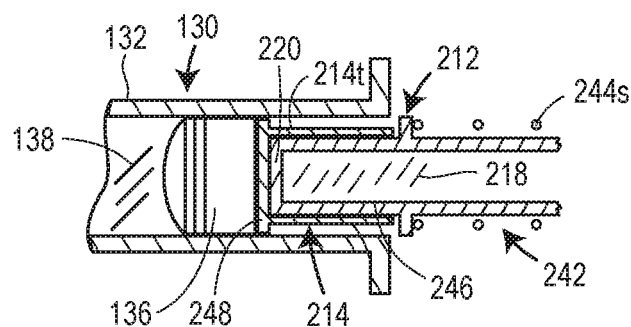

As shown in FIGS. 1, 2 and 3A-3C, the drive damper mechanism 170 can be disposed inline between the stopper 136 of the drug storage device 130 and the plunger head 148 of the plunger 142 to minimize the size of the injection device 100 and to more effectively damp the motion of plunger 142 at the plunger head/stopper interface. In other embodiments, as shown in FIGS. 4A-4C, the drive damper mechanism can be disposed inline between the proximal end of the plunger 142 of the injection drive mechanism and the cap 120 of the housing. In further embodiments, the drive damper mechanism can be integrated into the plunger 242, as shown in FIGS. 5A-5C.

In accordance with various embodiments of the injection device 100, the drive damper mechanism 170 may comprise a dashpot. The dashpot uses viscous friction to resist the motion of the plunger 142, thereby reducing the velocity of the plunger 142. FIGS. 2 and 3A-3C depict an exemplary embodiment of a linear dashpot 172 that can be used in the injection device 100. As shown, the dashpot 172 includes a housing 174, a working fluid 178 contained inside the housing 174, and a piston assembly 176 movably disposed within the housing 174. The housing 174 can comprise a cylindrical sidewall 174sw that is closed at each of its first and second ends by an end wall 174ew. In some embodiments, the housing 174 can be made of a rigid material, such as a plastic or a metal. The working fluid 178 contained within the housing 174 can comprise, without limitation, oil (e.g., mineral oil), silicone material, water or air.

Figure 2:
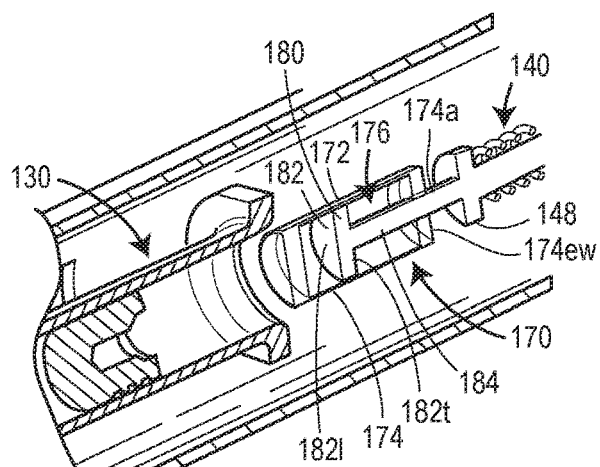
FIG. 2 is a cross-sectional perspective view of a section of the injection device showing an exemplary embodiment of a drive damping mechanism comprising a dashpot, which may be used in various embodiments of the injection device.

As shown in FIGS. 2 and 3A-3C, the piston assembly 176 may comprise a piston 180 and a rod 184 for pushing the piston 180 through the dashpot housing 174. In other embodiments, such as shown in FIGS. 4A-4C, the piston rod can be configured and adapted to pull the piston through the dashpot housing 194. As shown in FIG. 2, the piston 180 can comprise a single disc-like structure or member 182 (piston disc member 182) having leading and trailing surfaces 182l and 182t, respectively. The piston rod 184 extends through an aperture 174a in one of the end walls 174ew of the housing 174 and can have one end attached to or unitary with the leading surface 182l or trailing surface 182t of the piston disc member 182, depending upon whether it pushes (FIGS. 2 and 3A-3C) or pulls (FIGS. 4A-4C) the piston disc member 182 in the damping stroke. The free end of the piston rod 184, which is typically disposed external to the housing 174, can be attached to the plunger head 148, as shown in FIGS. 2 and 3A-3C. A seal, such as an O-ring (not visible), may be provided in or adjacent to the aperture 174a to prevent the working fluid 178 from leaking out of the housing 174 between the piston rod 184 and the aperture 174a in the end wall 174ew of the housing 174. In some embodiments, the piston assembly 176 of the injection device 100 can be made of a rigid material, such as a plastic or a metal. In other embodiments, the piston assembly 176 can be made of a resilient material, such as a natural or synthetic polymer. In still further embodiments, the piston assembly 176 can be made of a porous, rigid material.

Figure 3A:
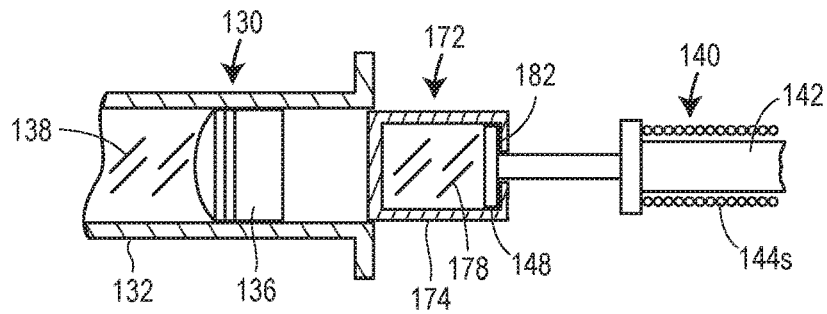
FIGS. 3A-3C are cross-sectional side views depicting an exemplary mode of operation of the dashpot and injection device of FIG. 2.
Figure 3B:
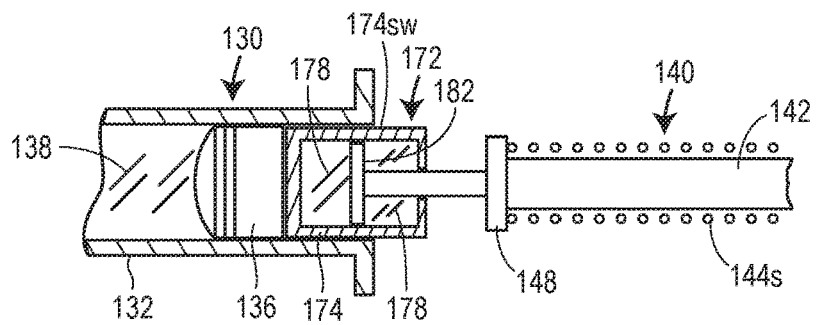
Figure 3C:
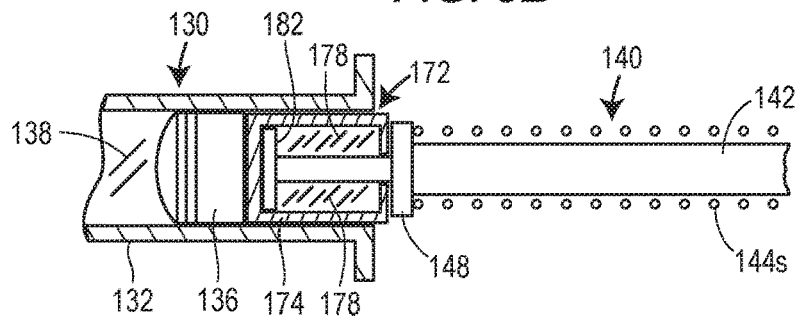
Figure 9A:
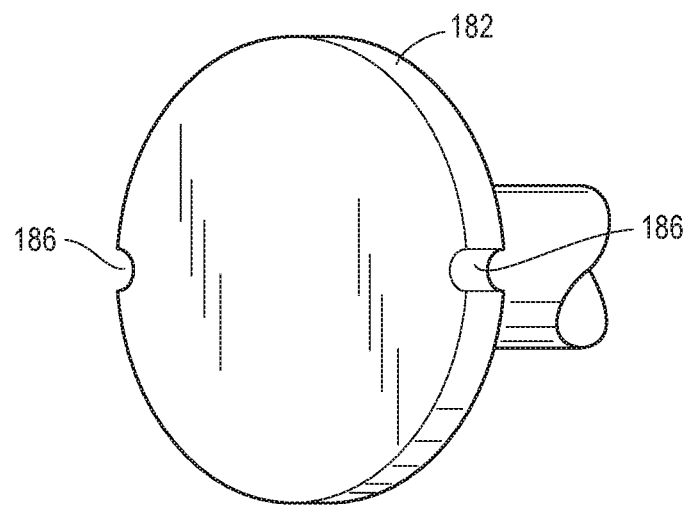
FIG. 9A is perspective view of an exemplary embodiment of a piston of the dashpot showing constrictions according to an exemplary embodiment of the present disclosure.
Figure 9B:
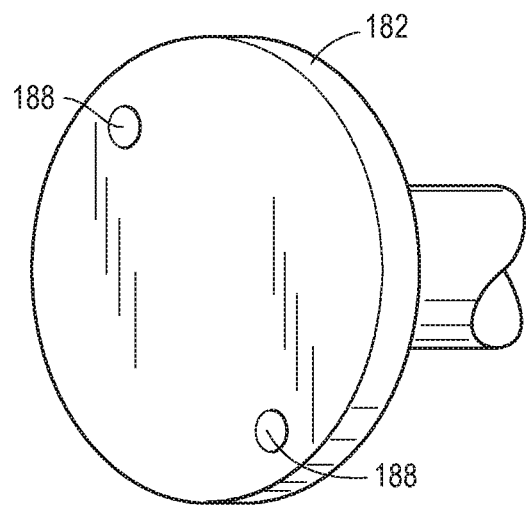
FIG. 9B is perspective view of another exemplary embodiment of the piston of the dashpot showing constrictions according to another exemplary embodiment of the present disclosure.

FIGS. 3A-3C depict one exemplary mode of operation of the dashpot 172 shown in FIG. 2. As shown in FIG. 3A, upon the actuation of the drive triggering mechanism, the energy source (e.g., spring 144s) of the injection drive mechanism 140 advances the plunger 142 toward stopper 136 disposed in the primary container 132 of the drug storage device 130. Once the dashpot 172 contacts the stopper 136, as shown in FIG. 3B, the load from the spring 144s begins to be transmitted to the dashpot 172, thereby causing the working fluid 178 located in front of the dashpot piston disc member 182 to be pushed or displaced through one or more constrictions to a location behind the piston disc member 182 as the piston disc member 182 moves from one end of the housing 174 to the other. The flow of the working fluid 178 through the one or more constrictions generates a viscous friction, which resists the movement of the piston disc member 182, thereby damping plunger motion. In some embodiments in which the piston disc member 182 is made of a rigid material, the constriction(s) can comprise a small gap (not shown) between the peripheral edge of the piston disc member 182 and the sidewall 174sw of the dashpot housing 174. In other embodiments, the constriction(s) further or alternatively comprise one or more grooves 186 provided in the peripheral edge of the piston disc member 182, as shown in FIG. 9A, and/or one or more openings 188 extending through the piston disc member 182 as shown in FIG. 9B, through which the working fluid 178 flows as it is displaced from in front of the piston disc member 182, to behind the piston disc member 182. In other embodiments in which the piston disc member 182 is made of a resilient material, the peripheral edge of the piston disc member 182 can bend backwards enough to generate a narrow gap or constriction between the peripheral edge of the piston disc member 182 and the sidewall 174sw of the dashpot housing 174 (not shown) so that the working fluid 178 can flow therethrough. In other embodiments in which the piston disc member 182 is made of a porous material, the working fluid 178 will flow through the pores (constrictions) of the piston disc member 182. In each of these embodiments, the one or more constrictions of the dashpot 172 provide a velocity-dependent resistance to the force of the energy source 144 (e.g., spring 144s) acting on the plunger 142. This resistance, when coupled to the plunger 142, reduces the velocity of the plunger 142 while maintaining the force of the energy source 144 (e.g., spring 144s) before the plunger 142 starts to move the stopper 136. The size, number and type of constrictions, the type of working fluid 178 used in the dashpot 172, the configuration of the housing 174 and piston assembly 176, and any combination thereof, can be adjusted and/or selected to allow the damping characteristics of the drive damper mechanism 170 to be tuned to properly damp the shock characteristics of the injection drive mechanism 140.

As shown in FIG. 3C, the piston disc member 182 engages the leading one of the end walls of the dashpot housing 174, and the force of the spring 144s moves the stopper 136, dashpot 172 and plunger 142 distally through the primary container 132 of the drug storage device 130 at a reduced velocity, to expel the drug 138 from the primary container 132.

FIGS. 4A-4C depict one exemplary mode of operation of a dashpot 192 disposed inline between the proximal end 146pe of the plunger rod 146 of the injection drive mechanism and the cap 120 of the outer casing of the injection device. In this embodiment, the dashpot housing 194 can be retained in the tubular support member 122 of the cap 120 of the outer casing by a detent 123 integrally formed with the tubular support member 122. Such an arrangement can be provided on a cantilever spring 125 defined in the tubular support member 122. The end of the piston rod 204 disposed within the dashpot housing 194 can be attached to the leading surface 202l of the piston disc member 202 and the free end of the piston rod 204 can be attached to the proximal end 146pe of the plunger rod 146 such that as the plunger rod 146 is driven distally by the energy source (e.g., spring 144s). The piston rod 204 pulls the piston disc member 202 through the dashpot housing 194.

As shown in FIGS. 4A-4C, upon the actuation of the drive triggering mechanism, the energy source (e.g., spring 144s) of the injection drive mechanism begins to advance the plunger 142 toward the stopper 136 disposed in the primary container 132 of the drug storage device 130. The load applied by the spring 144s to the plunger 142 can be transmitted to the dashpot 192. The working fluid 194 located in front of the piston disc member 202 is pushed or displaced through the one or more constrictions to a location behind the piston disc member 202, as the piston disc member 202 is pulled from one end of the dashpot housing 194 to the other. The resistance generated by the working fluid 198 flowing through the one or more constrictions maintains the force of the spring 144s while reducing the velocity of the plunger 142 before the head member of the plunger 142 impacts the stopper 136. The head member of the plunger 142 impacts the stopper 136 at the reduced velocity, and the force of the energy source (e.g., spring 144s) begins to move the stopper 136 and plunger 142 distally through the primary container 132 of the drug storage device 130, to expel the drug 138 from the primary container 132. At about the same time, the piston disc member 202 of the dashpot 192 reaches the end of its stroke and engages the leading end wall 194ew of the dashpot housing 194. The energy source (e.g., spring 144s) can be selected to apply enough energy to the plunger 142 to overcome the detent and cantilever arrangement 123/125 so that it releases the dashpot 192 from the tubular support member 122 of the outer casing cap 120 to allow for movement of the plunger 142 as the energy source (e.g., spring 144s) drives the plunger 142, stopper 136, and drug 138 through the primary container 132 of the drug storage device 130. The release of the dashpot 192 from the tubular support member 122 reduces the duration of engagement, which allows the overall length of the injection device to be reduced.

FIGS. 5A-5C depict an exemplary mode of operation of dashpot 212 that is integrated into plunger 242. As shown in FIGS. 5A-5C, the integrated dashpot 212 includes a housing 214 formed by a tubular wall 214t and plunger head 248, which closes the open distal end of the tubular wall 214t. The dashpot 212 further includes a piston formed by a distal end wall 220 of hollow plunger rod 246, which is initially disposed in the open proximal end of the tubular wall 214t of the dashpot housing 214. The working fluid 218 of the dashpot 212 is initially provided in the dashpot housing 214, in front of the distal end wall 220 of the plunger rod 246. As shown in FIG. 5A, upon actuation of the drive triggering mechanism (not shown), the energy source (e.g., spring 244s) of the injection drive mechanism applies a force to the plunger rod 246 and advances the plunger 242 toward stopper 136 disposed in the primary container 132 of the drug storage device 130. Once the plunger head 248 makes contact with the stopper 136, as shown in FIG. 5B, the load from the spring 244s is transmitted to the dashpot 212 integrally formed in the plunger 242. The working fluid 218 located in front of the end wall 220 of the plunger rod 246 is pushed or displaced through one or more constrictions (as previously described) provided in the end wall 220 and into the space defined by the hollow plunger rod 246, behind the end wall 220 as it moves distally into the dashpot housing 214. The resistance or damping provided by dashpot 212 reduces the velocity of the plunger rod 246 before the plunger rod 246 engages the plunger head 248 to move the stopper 136, and performs the damping while maintaining the force of the spring 244s.

As shown in FIG. 5C, the end wall 220 of the plunger rod 246 engages the plunger head 248, which marks the end of the damping stroke of the dashpot. The spring 244s then propels or forces the plunger rod 246 and plunger head 248 as a single component (i.e., the plunger) against the stopper 136 to drive the stopper 136 distally through the primary container 132 of the drug storage device 130, to expel the drug 138 from the primary container 132.

Figure 6:
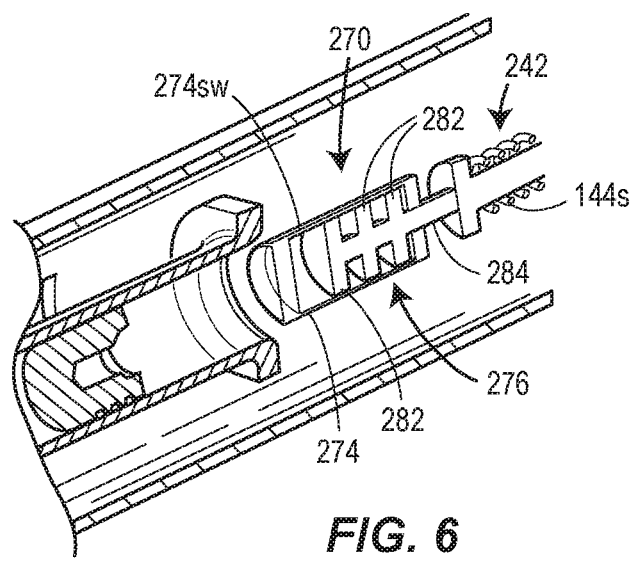
FIG. 6 is a cross-sectional perspective view of a section of the injection device showing another exemplary embodiment of a dashpot that may be used in various embodiments of the injection device.

FIG. 6 shows another exemplary embodiment of the dashpot. The dashpot 270 is substantially similar to the dashpots previously described except that the piston of the piston assembly 276 comprises two or more disc members 282 spaced apart from one another along the piston rod 284. The two or more piston disc members 282 and the previously described constrictions, which may be associated with each piston disc member 282, provide a series of resistances to piston movement, where each of the resistances can be the same and/or different. The series resistance of the dashpot 270 allows the velocity of the plunger to be reduced in stages or increments while maintaining the force of the energy source (e.g. spring 144s). In some embodiments, the multi-disc piston assembly 276 can be made of a rigid material, such as a plastic or a metal. In such embodiments, the constriction(s), which control or define the resistance provided by each piston disc member 282, can comprise a small gap (not shown) between the peripheral edge of one or more of the piston disc members 282 and the sidewall 274sw of the dashpot housing 274. In other such embodiments as shown in FIGS. 9A-9B, the constriction(s) can comprise one or more grooves 186 (FIG. 9A) provided in the peripheral edge of one or more of the piston disc members 182 or one or more openings 188 extending through the one or more piston disc members 182 (FIG. 9B), forming one or more of the piston disc members as porous discs, and any combination thereof. In other embodiments, the multi-disc piston assembly 276 can be made of a resilient material, such as a natural or synthetic elastomer, such that the marginal peripheral edge of each piston disc member 282 can bend backwards enough to generate a narrow gap or constriction between the peripheral edge of the piston disc members 282 and the sidewall 274sw of the dashpot housing 274 so that the working fluid can flow therethrough. If air is used as the working fluid, the resilient piston disc members 282 of the piston assembly 276 may be used to create a squeeze-film damping effect. Any of the dashpots described above with respect to FIGS. 2, 3A-3C, 4A-4C, and 5A-5C, can utilize the piston assembly 276 of FIG. 6.

Figure 7:
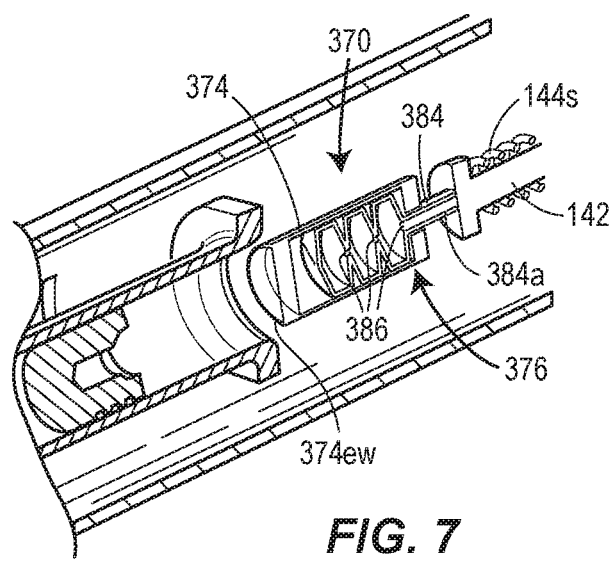
FIG. 7 is a cross-sectional perspective view of a section of the injection device showing a further exemplary embodiment of a dashpot that may be used in various embodiments of the injection device.

FIG. 7 shows an exemplary embodiment of the dashpot of the present invention. The dashpot 370 comprises a housing 374 and a piston assembly 376 comprising a hollow piston rod 384 and a piston configured as a bellows-like structure (bellows piston structure) attached to an end of the piston rod 384 disposed within the housing 374. The hollow piston rod 384 may have an aperture 384a for exhausting working fluid (not shown) flowing through the hollow piston rod 384 outside of the dashpot housing 374. The bellows piston structure can comprise one or more collapsible lobes that contain the working fluid, which fluid can be air or any other suitable working fluid. An opening 386 (constriction) can be provided in the portions of the lobe walls connecting each adjacent pair lobes of the bellows piston structure to one another and to the hollow piston rod 384. The openings 386 allow the working fluid contained in the lobes to flow from one lobe to another, thereby functioning as constrictions.

The dashpot 370 provides damping when the bellows piston structure is pushed or pulled into the end wall 374ew of the dashpot housing 374 and collapsed by the force acting on the plunger 142 supplied by the energy source (e.g., spring 144s) of the drive plunger mechanism. The damping action is provided as the working fluid contained inside the lobes flows through the openings 386, the hollow piston rod 384 and the rod aperture 384a as the lobes of the bellows piston structure are collapsed. Any of the dashpots embodiments described above with respect to FIGS. 2, 3A-3C, 4A-4C, and 5A-5C, can utilize the piston assembly 376 of FIG. 7.

Figure 8A:
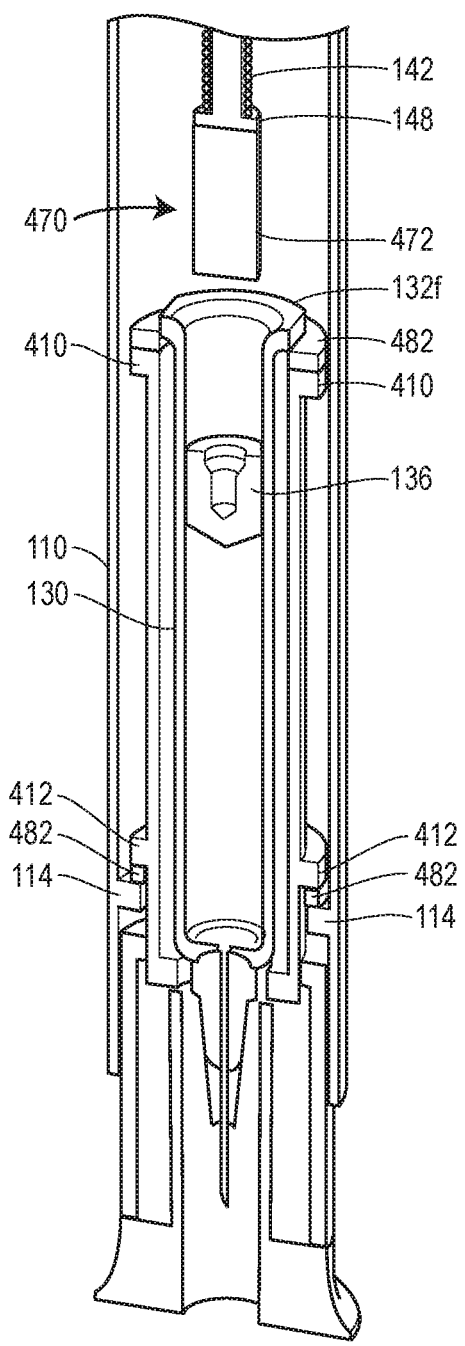
FIG. 8A is a cross-sectional perspective view of the injection device showing different exemplary embodiments of the drive damping mechanism.
Figure 8B:
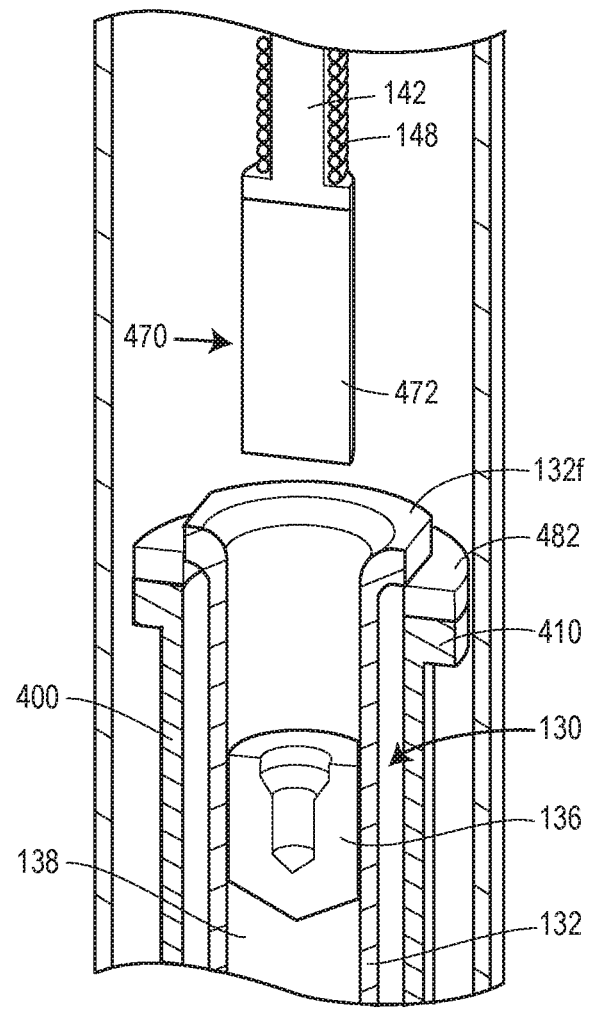
FIG. 8B is an enlarged view of a section of the injection device shown in FIG. 8A.

FIGS. 8A and 8B show an exemplary embodiment of the drive damper mechanism of the present invention. In this embodiment, the drive damper mechanism 470 can comprise an elongated strip of energy absorbing or damping material 472 attached to the head member 148 of the plunger 142. Damping is provided when the strip of damping material 472 attached to the head member 148 of the plunger 142 impacts the stopper 136 disposed in the primary container 132 of the drug storage device 130 and compresses to absorb the force supplied by the energy source (e.g., spring 144s) to the plunger 142, thereby providing hysteretic damping of the plunger 142, which reduces the velocity of the plunger 142. The damping material can comprise a single layer of damping material or be a laminate formed by two or more layers of damping material. In some embodiments, the two or more layers of damping material can be bonded to one another. In other embodiments, the two or more layers of damping material are not bonded to one another. One or more layers of the damping material can be made from a visco-elastic material or a synthetic porous material (e.g., an aerogel). The layers of the laminate damping material can have the same or different damping characteristics to tune the damping characteristics of the drive damper mechanism 470 to properly damp the shock characteristic of the drive plunger mechanism. In various embodiments, one or more layers of damping material can be made from a thermoplastic visco-elastomeric material sold under the trademark ISODAMP® and manufactured by Aearo E-A-R Specialty Composites.

Figure 10:
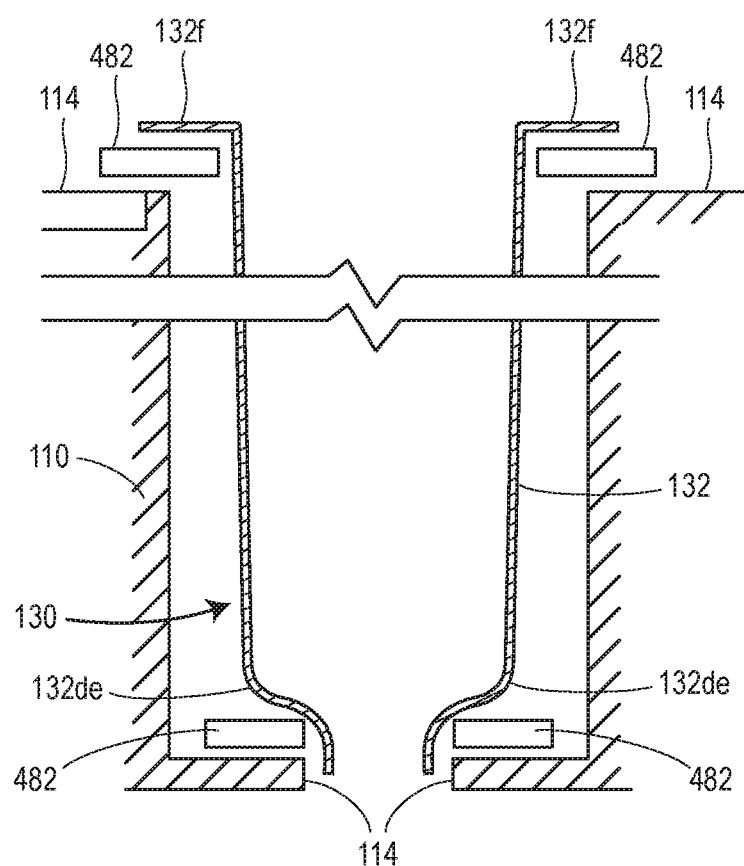
FIG. 10 is a cross-sectional view of a section of the injection device showing another exemplary embodiment of a drive damping mechanism.

Referring to FIG. 10, some embodiments of the injection device can further or alternately include a drive damper mechanism that comprises a strip of energy absorbing or damping material 482 disposed between each portion of the primary container 132 of the drug storage device 130, which engages or contacts one of the support members 114 of the outer casing 110. As shown in FIG. 10, the damping material 482 can be disposed between flange 132f and support member(s) 114 and between the closed distal end 132de of the primary container 132 and support member(s) 114. In other embodiments, strips of damping material can be disposed at various locations between the interior surface of the outer casing 110 and the primary container 132. Damping is provided because the strips of damping material 482 compress to absorb the force caused by the plunger impacting the stopper, which force is supplied by the energy source. In some embodiments, the damping material can be made from a visco-elastic material or an aerogel. In some embodiments, the damping material can comprise a single layer of damping material or be a laminate formed by two or more layers of damping material bonded to one another. The layers of the laminate can have the same or different damping characteristics to tune the damping characteristics of the drive damper mechanism to properly damp the shock characteristic of the drive plunger mechanism. In various embodiments of the present invention, one or more layers of the damping material can be made from a thermoplastic visco-elastomeric material sold under the trademark ISODAMP® and manufactured by Aearo E-A-R Specialty Composites.

Referring again to FIGS. 8A and 8B, the drug storage device 130 may be mounted in a holding sleeve 400 that can be provided within the outer casing 110. The holding sleeve 400 can include a container support flange 410 for supporting the primary container 132 of the drug storage device 130 and a casing engagement flange 412 for engaging one or more of the support members 114 of the casing 110. Strips 482 of energy absorbing or damping material, similar to the strips described above, can be used between the drug storage device 130 and the holding sleeve 400 and/or between the casing 110 and the holding sleeve 400 to damp the plunger/stopper forces applied to the drug storage device 130 and the drug 138 stored in the primary container 132 of the drug storage device 130. In the embodiment shown, a first strip 482 of energy absorbing or damping material can be disposed between the container support flange 410 of a holding sleeve 400 and the rim flange 132f of the primary container 132 of the drug storage device 130. A second strip 482 of energy absorbing or damping material can be disposed between the casing engagement flange 412 of the holding sleeve 400 and the support member 114 of the outer casing 110. Further embodiments of the injection device may include strips of energy absorbing or damping material disposed between the primary container 132 and the holding sleeve 400 and/or between the holding sleeve 400 and the outer casing 110, and/or at other points of contact within the injection device.

The above description describes various systems and methods for use with a drug delivery device. It should be clear that the system, drug delivery device or methods can further comprise use of a drug or medicament listed below with the caveat that the following list should neither be considered to be all-inclusive nor limiting. The medicament will be contained in a reservoir. In some instances, the reservoir is the primary container that is either filled or pre-filled for treatment with the medicament. The primary container can be a cartridge or a pre-filled syringe.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgrastim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO: 2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of SEQ ID NOS: 305-351, including TN8-19-1 through TN8-19-40, TN8-19 con1 and TN8-19 cont; peptibodies of the mL2 family of SEQ ID NOS: 357-383; the mL15 family of SEQ ID NOS: 384-409; the mL17 family of SEQ ID NOS: 410-438; the mL20 family of SEQ ID NOS: 439-446; the mL21 family of SEQ ID NOS: 447-452; the mL24 family of SEQ ID NOS: 453-454; and those of SEQ ID NOS: 615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2×L1(N); 2×L1(N) WT; Con4 (N), Con4 (N) 1K WT, 2×Con4 (N) 1K; L1C; L1C 1K; 2×L1C; Con4C; Con4C 1K; 2×Con4C 1K; Con4-L1 (N); Con4-L1C; TN-12-9 (N); C17 (N); TN8-8(N); TN-8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AblA1; AblF; AblK, AblP; and AblP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of SEQ ID NO: 17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO: 8 and a light chain variable region having SEQ ID NO: 6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti- CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-C. difficile Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/1L23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9), e.g. U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, a bispecific T cell engager antibody (BiTe), e.g. Blinotumomab can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

Although the drug injection device, drive damper mechanisms, systems, methods, and elements thereof, have been described in terms of exemplary embodiments, they are not limited thereto. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention.

It should be understood that the legal scope of the invention is defined by the words of the claims set forth at the end of this patent. The appended claims should be construed broadly to include other variants and embodiments of same, which may be made by those skilled in the art without departing from the scope and range of equivalents of the device, drive damper mechanisms, systems, methods, and their elements.

What is claimed is:

1. An injection device for drug delivery, the injection device comprising:
  a container for storing a drug, the container comprising a stopper movably disposed in the container for expelling the drug;
  an injection drive mechanism comprising a plunger for acting on the stopper and an energy source for exerting a force on the plunger to cause the plunger to act on the stopper to expel the drug, the force causing the plunger to accelerate to a velocity prior to acting on the stopper; and
  a damping mechanism for reducing the velocity of the plunger prior to the plunger acting on the stopper, the damping mechanism comprising a housing, a piston assembly acted upon by the plunger to be movable in the housing between a first position spaced from an end wall of the housing and a second position engaging the end wall of the housing, and a working fluid displaceable by the piston assembly for resisting movement of the plunger;

wherein the plunger acting on the stopper to expel the drug corresponds to the piston assembly being in the second position.

2. The injection device of claim 1, wherein the damping mechanism is (a) disposed between the stopper and the plunger, (b) disposed at an end of the plunger which is opposite to the stopper, or (c) integral with the plunger.

3. The injection device of claim 1, wherein the piston assembly includes a piston and a rod for pushing or pulling the piston.

4. The injection device of claim 3, wherein the piston assembly includes a disc-shaped piston.

5. The injection device of claim 4, wherein (a) the piston is rigid, (b) the piston is resilient, or (c) the piston is porous.

6. The injection device of claim 5, wherein the piston includes at least one constriction (a) in a peripheral edge of the piston or (b) in the piston.

7. The injection device of claim 3, wherein the piston assembly includes a piston comprising two or more disc-shaped members or a bellows structure.

8. The injection device of claim 1, further comprising an outer casing for encasing the container, the outer casing including at least one support member for holding container within the outer casing, and energy absorbing material disposed between the at least one support member and the container.

9. The injection device of claim 1, further comprising a drug stored in the container.

10. The injection device of claim 9, wherein the drug is selected from the group consisting of TNF inhibitors, antibodies to the calcitonin gene-related peptide receptor, colony stimulating factors, a granucolyte colony-stimulating factor, erythropoiesis stimulating agents, apelin receptor agonists, anti-thymic stromal lymphopoietin antibodies, anti-thymic stromal lymphopoietinreceptor antibodies, antibodies that bind human Proprotein Convertase Subtilisin/Kexin Type 9 and tissue inhibitors of metalloproteinases.

11. A damper mechanism for an injection device having a drug storage container including a stopper movably disposed in the container, and a plunger for acting on the stopper, the damping mechanism for reducing a velocity of the plunger prior to acting on the stopper, the damper mechanism comprising:

a housing having an end wall with an inner surface facing the stopper;

a piston assembly movable in the housing between a first position spaced from the inner surface of the end wall of the housing and a second position engaging the inner surface of the end wall of the housing and acted upon by a plunger of the injection device; and a working fluid displaceable by the piston assembly for resisting movement of the plunger;

wherein the piston assembly being disposed in the second position causes the plunger to act on the stopper to move the stopper within the container.

12. The damper mechanism of claim 11, wherein the damping mechanism is integral with the plunger.

13. The damper mechanism of claim 11, wherein the piston assembly includes a piston and a rod for pushing or pulling the piston.

14. The damper mechanism of claim 13, wherein the piston assembly includes a disc-shaped piston.

15. The damper mechanism of claim 14, wherein (a) the piston is rigid, (b) the piston is resilient, or (c) the piston is porous.

16. The damper mechanism of claim 15, wherein the piston includes at least one constriction (a) in a peripheral edge of the piston or (b) in the piston.

17. The damper mechanism of claim 13, wherein the piston assembly includes a piston comprising two or more disc-shaped members.

18. The damper mechanism of claim 13, wherein the piston assembly includes a piston comprising a bellows structure.

19. The damper mechanism of claim 18, wherein the bellows structure includes at least two lobes and a constriction for allowing the working fluid to flow between the two lobes or the rod is hollow to allow the working fluid to be exhausted from the bellows structure.

20. A method for administering a drug comprising:

providing a container containing a drug and a stopper movably disposed in the container for expelling the drug;

acting on the stopper with a plunger driven by an energy source that exerts a force on the plunger, the force causing the plunger to accelerate to a velocity prior to acting on the stopper; and reducing the velocity of the plunger with a damping mechanism prior to acting on the stopper, the damping mechanism comprising a piston assembly movable in a housing between a first position spaced from an end wall of the housing and a second position engaging the end wall of the housing and acted upon by the plunger, and a working fluid displaceable by the piston assembly for resisting movement of the plunger;

wherein acting on the stopper with the plunger comprises driving the stopper within the container with the piston assembly in the second position.

21. The method of claim 20, further comprising expelling the drug, which is selected from the group consisting of TNF inhibitors, antibodies to the calcitonin gene-related peptide receptor, colony stimulating factors, a granucolyte colony stimulating factor, erythropoiesis stimulating agents, apelin receptor agonists, anti-thymic stromal lymphopoietin antibodies, anti-thymic stromal lymphopoietinreceptor antibodies, antibodies that bind human Proprotein Convertase Subtilisin/Kexin Type 9 and tissue inhibitors of metalloproteinases.

22. The method of claim 20, wherein the damping mechanism (a) is disposed between the stopper and the plunger, (b) is disposed at an end of the plunger which is opposite to the stopper, or (c) is integral with the plunger.

23. The method of claim 20, wherein the piston assembly includes a piston and a rod for pushing or pulling the piston.

24. The method of claim 23, wherein the piston assembly includes at least one disc-shaped piston.

25. The method of claim 24, wherein (a) the piston is rigid, (b) the piston is resilient, or (c) the piston is porous.

26. The method of claim 25, wherein the piston includes at least one constriction (a) in a peripheral edge of the piston or (b) in the piston.

27. The method of claim 23, wherein the piston assembly includes a piston comprising a bellows structure.

28. The method of claim 27, wherein the bellows structure includes at least two lobes and a constriction for allowing the working fluid to flow between the two lobes.

29. The method of claim 20, further comprising an outer casing for encasing the container, the outer casing including at least one support member for holding container within the outer casing, and energy absorbing material disposed between the at least one support member and the container.

30. The method of claim 20, wherein the damping mechanism comprises the piston assembly movable in the housing between the first position spaced from a distalmost wall of the housing, perpendicular to a longitudinal axis of the housing and the second position engaging the distalmost wall of the housing and acted upon by the plunger.

31. The injection device of claim 1, wherein the damping mechanism comprises the housing, the piston assembly acted upon by the plunger to be movable in the housing between the first position spaced from a distalmost wall of the housing, perpendicular to a longitudinal axis of the housing and the second position engaging the distalmost wall of the housing, and the working fluid displaceable by the piston assembly for resisting movement of the plunger.

32. The damper mechanism of claim 11, wherein the end wall of the housing comprises a distalmost wall of the housing, perpendicular to a longitudinal axis of the injection device; and the piston assembly is movable in the housing between the first position spaced from the distalmost wall of the housing and the second position engaging the distalmost wall of the housing and acted upon by the plunger of the injection device.

\* \* \* \* \*